(12) United States Patent
Baratian et al.

(10) Patent No.: US 7,105,716 B2
(45) Date of Patent: Sep. 12, 2006

(54) ABSORBENT ARTICLES

(75) Inventors: Stephen Baratian, Roswell, GA (US); Christopher Dale Fenwick, Alpharetta, GA (US); Melpo Lambidonis, Cumming, GA (US); Susan Carol Sudbeck, Alpharetta, GA (US); Christian Trusock, Cumming, GA (US); James Hongxue Wang, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 117 days.

(21) Appl. No.: 10/749,627

(22) Filed: Dec. 31, 2003

(65) Prior Publication Data

US 2005/0148967 A1    Jul. 7, 2005

(51) Int. Cl.
 *A61F 13/15*    (2006.01)
(52) U.S. Cl. .............. 604/367; 604/384; 604/385.101
(58) Field of Classification Search ........... 604/385.01, 604/385.101, 383, 380, 378, 367, 358, 372, 604/384; 442/384
See application file for complete search history.

(56) References Cited

U.S. PATENT DOCUMENTS

| | | | | |
|---|---|---|---|---|
| 1,829,231 A | * | 10/1931 | Mergentime | 66/170 |
| 2,627,644 A | * | 2/1953 | Foster | 428/175 |
| 2,902,038 A | * | 9/1959 | Bletzinger et al. | 604/365 |
| 3,150,693 A | * | 9/1964 | Seltzer | 139/383 R |
| 3,236,238 A | * | 2/1966 | Morse | 604/366 |
| 3,338,992 A | | 8/1967 | Kinney | |
| 3,341,394 A | | 9/1967 | Kinney | |
| 3,367,333 A | * | 2/1968 | Scheier | 604/375 |
| 3,491,802 A | * | 1/1970 | Olderman et al. | 139/420 R |
| 3,498,296 A | * | 3/1970 | Gallagher | 604/372 |
| 3,502,538 A | | 3/1970 | Petersen | |
| 3,502,763 A | | 3/1970 | Hartmann | |
| 3,542,615 A | | 11/1970 | Dobo et al. | |
| 3,592,194 A | | 7/1971 | Duncan | |
| 3,692,618 A | | 9/1972 | Dorschner et al. | |
| 3,802,817 A | | 4/1974 | Matsuki et al. | |
| 3,849,241 A | | 11/1974 | Butin et al. | |
| 4,037,601 A | * | 7/1977 | Denkinger | 604/366 |
| 4,041,951 A | | 8/1977 | Sanford | |
| 4,324,246 A | * | 4/1982 | Mullane et al. | 604/366 |
| 4,340,563 A | | 7/1982 | Appel et al. | |
| 4,637,819 A | | 1/1987 | Ouellette et al. | |
| 4,690,679 A | * | 9/1987 | Mattingly et al. | 604/383 |
| 4,710,185 A | * | 12/1987 | Sneyd et al. | 604/372 |
| 4,723,953 A | * | 2/1988 | Rosenbaum et al. | 604/369 |
| 4,761,322 A | | 8/1988 | Raley | |

(Continued)

FOREIGN PATENT DOCUMENTS

EP    0007665    2/1980

(Continued)

OTHER PUBLICATIONS

ASTM Designation: D 737-96, "Standard Test Method for Air Permeability of Textile Fabrics", Published Apr. 1996, pp. 207-211.

*Primary Examiner*—Tatyana Zalukaeva
*Assistant Examiner*—Paula L. Craig
(74) *Attorney, Agent, or Firm*—Christos S. Kyriakou; David J. Arteman (57) ABSTRACT

The present invention provides an improved disposable article for the absorption and containment of urine or other body exudates, for example a diaper, training pants or an adult incontinence article, that has a high fecal fluid intake rate as measured by the Fecal Fluid Intake Test.

9 Claims, 3 Drawing Sheets

U.S. PATENT DOCUMENTS

| | | | |
|---|---|---|---|
| 4,781,962 A | 11/1988 | Zamarripa et al. | |
| 5,158,821 A | 10/1992 | Gebauer et al. | |
| 5,192,606 A * | 3/1993 | Proxmire et al. | 428/171 |
| 5,364,686 A | 11/1994 | Disselbeck et al. | |
| 5,527,300 A * | 6/1996 | Sauer | 604/378 |
| 5,531,727 A | 7/1996 | Cohen et al. | |
| 5,536,555 A * | 7/1996 | Zelazoski et al. | 428/138 |
| 5,540,872 A | 7/1996 | Ulman | |
| 5,643,653 A * | 7/1997 | Griesbach et al. | 428/120 |
| 5,670,110 A * | 9/1997 | Dirk et al. | 264/504 |
| 5,731,062 A | 3/1998 | Kim et al. | |
| 5,820,615 A | 10/1998 | Koczab | |
| 5,824,352 A * | 10/1998 | Yang et al. | 425/290 |
| 5,851,930 A | 12/1998 | Bessey et al. | |
| 5,896,680 A * | 4/1999 | Kim et al. | 36/28 |
| 5,904,675 A | 5/1999 | Laux et al. | |
| 5,925,026 A * | 7/1999 | Arteman et al. | 604/383 |
| 5,931,823 A * | 8/1999 | Stokes et al. | 604/358 |
| 5,986,167 A * | 11/1999 | Arteman et al. | 604/380 |
| 5,990,377 A * | 11/1999 | Chen et al. | 604/381 |
| 6,007,898 A | 12/1999 | Km et al. | |
| 6,015,936 A * | 1/2000 | Takai et al. | 604/383 |
| 6,022,818 A * | 2/2000 | Welchel et al. | 442/384 |
| 6,117,524 A * | 9/2000 | Hisanaka et al. | 428/137 |
| 6,269,504 B1 | 8/2001 | Romano et al. | |
| 6,286,167 B1 | 9/2001 | Stolpmann | |
| 6,316,687 B1 | 11/2001 | Davis et al. | |
| 6,395,957 B1 | 5/2002 | Chen et al. | |
| 6,506,959 B1 | 1/2003 | Hamajima et al. | |
| 6,515,029 B1 | 2/2003 | Krzysik et al. | |
| 6,635,799 B1 | 10/2003 | Osborn, III et al. | |
| 6,673,418 B1 | 1/2004 | DeOlivera et al. | |
| 6,696,618 B1 * | 2/2004 | Dodge et al. | 604/367 |
| 6,727,404 B1 * | 4/2004 | Ruman et al. | 604/378 |
| 6,803,334 B1 * | 10/2004 | Mizutani et al. | 442/394 |
| 2001/0044614 A1 * | 11/2001 | Damay et al. | 604/385.01 |
| 2001/0054200 A1 | 12/2001 | Romano et al. | |
| 2002/0099347 A1 | 7/2002 | Chen et al. | |
| 2002/0103469 A1 | 8/2002 | Chen et al. | |
| 2002/0107495 A1 | 8/2002 | Chen et al. | |
| 2003/0124311 A1 | 7/2003 | Cree et al. | |
| 2003/0135967 A1 | 7/2003 | Putnam et al. | |
| 2003/0167044 A1 * | 9/2003 | Toyoshima et al. | 604/367 |
| 2003/0167548 A1 | 9/2003 | LaShoto et al. | |
| 2003/0167557 A1 | 9/2003 | LaShoto et al. | |
| 2003/0191442 A1 | 10/2003 | Bewick-Sonntag et al. | |
| 2003/0203162 A1 * | 10/2003 | Fenwick et al. | 428/156 |
| 2003/0203691 A1 * | 10/2003 | Fenwick et al. | 442/327 |
| 2003/0208175 A1 * | 11/2003 | Gross et al. | 604/378 |
| 2003/0224146 A1 | 12/2003 | Raidel et al. | |
| 2004/0016091 A1 | 1/2004 | Rivera et al. | |
| 2004/0265533 A1 * | 12/2004 | Hoying et al. | 428/92 |

FOREIGN PATENT DOCUMENTS

| | | |
|---|---|---|
| EP | 0 358 031 B1 | 1/1995 |
| EP | 0 705 354 B1 | 6/1997 |
| EP | 0 930 861 B1 | 1/2002 |
| EP | 1 124 520 B1 | 6/2003 |
| EP | 1 137 382 B1 | 6/2003 |
| JP | 11-81116 A | 3/1999 |
| JP | 11-89877 A | 4/1999 |
| JP | 11-286863 A | 10/1999 |
| WO | WO 94/25658 | 11/1994 |
| WO | WO 98/49381 | 11/1998 |
| WO | WO 98/58109 | 12/1998 |
| WO | WO 99/09922 | 3/1999 |
| WO | WO 99/25283 | 5/1999 |
| WO | WO 03/26183 | 3/2003 |
| WO | WO 03/093554 A2 | 11/2003 |
| WO | WO 03/093558 A1 | 11/2003 |

* cited by examiner

ABSORBENT ARTICLES

FIELD OF THE INVENTION

The invention relates to disposable articles for the absorption and containment of urine or other body exudates.

BACKGROUND OF THE INVENTION

Personal care absorbent articles, such as diapers, training pants, and adult incontinence garments typically include a liquid pervious top layer (often referred to as a bodyside liner or topsheet), a liquid impermeable bottom layer (often referred to as an outer cover), and an absorbent core between them. The absorbent core is often defined as including a front region (closer to the front waist of the wearer), a back region (closer to the rear waist of the wearer), and a crotch region (the lowermost region on a wearer, connecting the front region to the back region). For purposes of this document, the front region of the absorbent core may be defined as including one-third of the length of the absorbent core measured from the edge of the absorbent core which is closest to the front waist edge of the article. The back region of the absorbent core may be defined as including one-third of the length of the absorbent core measured from the edge of the absorbent core which is closest to the rear waist edge of the article. The crotch region of the absorbent core may be defined as including the remaining one-third of the length of the absorbent core which is bounded by the front region and the back region.

Conventional bodyside liner materials are liquid pervious layers constructed of a nonwoven fabric such as a spunbonded layer of polypropylene spunbonded fibers. Bodyside liners are designed to provide a liquid pervious barrier between a wearer of a personal care absorbent article that includes the liner and any absorbent structures beneath the liner. With this in mind, it is known to provide bodyside liners which are liquid pervious and that do not retain liquids. Such liners merely act as a pass through or separation layer. The structure of such bodyside liners is optimized primarily based on providing liquid intake and dryness, mostly with respect to urine. Conventional bodyside liners do not permit the intake of fecal matter, particularly runny fecal matter.

In addition to urine, absorbent articles are also subjected to insults of runny fecal matter. Although efforts have been made to absorb, contain, or otherwise entrap runny fecal matter, conventional bodyside liners do not provide sufficient intake of runny fecal matter and do not limit the spread of runny fecal matter. Consequently, runny fecal matter has a greater tendency to spread and leak, than does urine, from conventional absorbent articles.

SUMMARY OF THE INVENTION

In one embodiment, the present invention provides a disposable absorbent article for the absorption and containment of urine or other body exudates that has a fecal fluid intake rate of greater than about 1.2 cubic centimeters per second as measured by the Fecal Fluid Intake Test. In another embodiment, the disposable absorbent article has a fecal fluid intake rate of at least about 1.3 cubic centimeters per second as measured by the Fecal Fluid Intake Test. In yet another embodiment, the disposable absorbent article has a fecal fluid intake rate of at least about 1.4 cubic centimeters per second as measured by the Fecal Fluid Intake Test. The fecal fluid intake rate may be at least about 1.5 cubic centimeters per second, at least about 2 cubic centimeters per second and even at least about 2.5 cubic centimeters per second as measured by the Fecal Fluid Intake Test. The liquid pervious bodyside liner may include a portion that has a air permeability of greater than about 3000 cubic feet per minute as measured by ASTM D 737-96 at 125 Pascals.

In certain embodiments, at least a portion of the liquid pervious bodyside liner of the disposable absorbent article includes a plurality of pores having at least one dimension greater than about 0.25 millimeters wherein the total open area of the plurality of pores comprises greater than about 30 percent of the total surface area of the liquid pervious bodyside liner. In certain embodiments, at least a portion of the liquid pervious bodyside liner of the disposable absorbent article includes a plurality of pores having at least one dimension greater than about 0.5 square millimeters and the total open area of the plurality of pores comprise greater than about 30 percent of the total surface area of the liquid pervious bodyside liner. In certain embodiments, at least a portion of the liquid pervious bodyside liner comprises at least one topographical feature having a height of greater than about 2.5 millimeters, more desirably, a plurality of topographical feature having heights of greater than about 5 millimeters. In certain embodiments, the disposable absorbent article includes topographical features that maintain at least 0.08 cubic centimeters of air space, per square centimeter of liquid pervious bodyside liner between the top surface of the bodyside liner and an article resting on the macroscopic surface feature at a 0.3450 kPa load on the web.

The disposable absorbent article may include a portion that is characterized by a flowback of less than about 0.053 grams as measured by the Fecal Fluid Flowback Test. The disposable absorbent article may include a portion that is characterized by a flowback of less than about 0.052 grams and even less than about 0.051 grams as measured by the Fecal Fluid Flowback Test. Desirably, the percentage of surface area of the portion of bodyside liner that contacts the skin under a 0.3450 kPa load is less than about 40 percent of the area of the bodyside liner. More desirably, the percentage of surface area of the portion of bodyside liner that contacts the skin under a 0.3450 kPa load is less than about 30 percent of the bodyside liner. Still more desirably, the percentage of surface area of the portion of bodyside liner that contacts the skin under a 0.3450 kPa load is less than about 25 percent of the area of the bodyside liner. The disposable absorbent article may be a diaper, an adult incontinence article, or a training pant.

The present invention also provides a diaper having a high fecal fluid intake rate as measured by the Fecal Fluid Intake Test and a TEWL less than about 17 grams per square meter per hour as measured by the Skin Hydration Test. The TEWL may be less than about 16 grams per square meter per hour as measured by the Skin Hydration Test or even less than about 15.5 grams per square meter per hour as measured by the Skin Hydration Test.

DEFINITIONS

Within the context of this specification, each term or phrase below will include the following meaning or meanings.

"Absorbent article" includes without limitation diapers, training pants, swim wear, absorbent underpants, baby wipes, adult incontinence products, feminine hygiene products, and protective garments including without limitation medical garments, underpads, bandages, absorbent drapes, and medical wipes, as well as industrial work wear garments.

The term "absorbent core system" comprises of a liquid pervious liner, a surge, and an absorbent core.

The term "absorbent core" refers to the material primarily responsible for absorbing and retaining body fluids such as urine, menses, etc. Absorbent core usually comprises of a superabsorbent material and/or a fibrous material such as pulp fluff.

The term "superabsorbent material" refers to water-swellable organic and inorganic materials that are capable of absorbing at least 15 times their own weight in synthetic and/or that are capable of absorbing at least 15 times their own weight in 0.9 weight percent saline solution.

The term "personal care absorbent article" includes without limitation diapers, training pants, swim wear, absorbent underpants, adult incontinence products, tissues, wet wipes, bed mats, and feminine hygiene articles.

"Liquid impervious," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid pervious material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Nonwoven" and "nonwoven web" refer to materials and webs of material which are formed without the aid of a textile weaving or knitting process.

"Meltblown nonwoven" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Polymers" include, but are not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic tacticities.

"Spunbonded nonwoven" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Surge" and "surge material" refer to a material designed primarily to receive, temporarily store, and/or transport liquid in an absorbent article along a mutually facing surface with an absorbent assembly designed to store liquid within the absorbent article.

These terms may be defined with additional language in the remaining portions of the specification.

Test Methods

Procedure for Skin Hydration Test

Skin hydration values are determined by measuring TransEpidermal Water Loss (TEWL) and can be determined by employing the following test procedure. The test is conducted on adults on the forearm. Any medications should be reviewed to ensure they have no effect on test results and the subject's forearms should be free of any skin conditions such as rashes or abrasions. Subjects should relax in the test environment, which should be at about 72° F. (22° C.) with a humidity of about 40 percent, for about 15 minutes prior to testing and movement should be kept to a minimum during testing. Subjects should wear short sleeve shirts, not bathe or shower for about 2 hours before testing, and should not apply any perfumes, lotions, powders, etc., to the forearm.

The measurements are taken with an evaporimeter, such as a DERMALAB® instrument distributed by Cortex Technology, Textilvaenget 1 9560 Hadsund Denmark.

A baseline reading should be taken on the subject's midvolar forearm and should be less than 10 g/m$^2$/hr. Each test measurement is taken over a period of two minutes with TEWL values taken once per second (a total of 120 TEWL values).

The end of a dispensing tube is placed on the mid-forearm for carrying out the test. The eye of the tube should be facing the target loading zone. A product to be tested is placed on the subject's forearm directly over the end of the tube. The product may vary depending upon the type of material to be tested or material availability so care should be taken to ensure that test results are comparable. A stretchable net such as that available from, Sturgilast Tublar Elastic Dressing Retainer Western Medical should be placed over the product to help to hold it in place.

Three equal loadings of 70 ml of 0.9 weight percent of NaCl aqueous solution available from VWR Scientific Products at about 95° F.+/−5° F. (35° C.) are delivered to the product at an interval of 45 seconds at a rate of 300 mils/minute by a pump such as a MASTERFLEX LS® pump. After 60 minutes, the product is removed from the subject's forearm and Evaporimeter readings taken immediately on the skin at the subject's midvolar forearm where the product had been. TransEpidermal Water Loss values are reported as the difference between the one hour and baseline values in $g/m^2/hr$.

Preparation of Synthetic Fecal Fluid

In order to develop a successful fecal fluid simulant, the resultant fecal fluid simulant should have key properties similar to those of the real fecal fluid. But the real biological fecal fluids have huge inherent variations. The feces of infants vary substantially depending on the type of food and among infants. The infants on formula produce feces of much higher viscosity than the infants on mother's breast milk. To obtain the bowel movement (hereinafter BM) properties of runny BM, a number of infants on breast milk were recruited. Their feces were colleted with a special diaper with a BM collection bag. The collected samples were tested for their viscosity, liner penetration rates and other properties.

A. Determination of the Fecal Fluid Targets:

1. Separation of Infant BM

In order to determine the target for fecal fluid simulant, it was important to separate the fecal fluid from the collected BM samples and then the properties of fecal fluid can be determined. To accomplish this, a centrifuge separation method was used. This method worked well. It resulted in two fractions, a solid fraction and a fecal fluid fraction. The fecal fluid fraction was collected and subjected to the analysis of chemical compositions and testing of its interaction with superabsorbent. A total of nineteen fecal fluid samples were collected in a six-week period.

2. Composition of Fecal Fluid

Nineteen collected fecal fluid samples were frozen and analyzed for composition. Samples of several whole BM samples were also analyzed for internal control. The following results were found:

Protein: Average, 1.99%; Standard Deviation: 0.44%; Range, 1.48 to 2.83%

Carbohydrates: Average, 6.84%; Standard Deviation, 2.11%; Range, 4.7 to 11.3%

Fat: Average, 0.11%; Standard Deviation, 0.21%; Range, 0.01 to 11.3%

Water: Average, 90.82%; Standard Deviation, 2.3%; Range, 85.84 to 93.48%

The compositional data were used to determine the effects of these fecal fluid components on the absorbency of superabsorbents and develop a fecal fluid simulant.

3. Absorbency of Collected Fecal Fluid

The absorbency of fecal fluid was determined using the fecal fluid absorbency under load (AUL) method at 0.3 psi, described below. The fecal fluid samples did not contain any particles but have dissolved proteins, carbohydrates, and a very small amount of fat. The viscosity of the collected fecal fluid is under 1 poise.

The screen porosity of the AUL calendar was found to be important to obtain reproducible results. The 100-mesh screen was found to be effective. A 400-mesh screen was found to be too fine for obtaining reproducible results partly caused by the increased resistance to the transport of fecal fluid through the small pores on the screen.

Fourteen collected fecal fluid samples were tested for 0.3 psi AUL. A Stockhausen superabsorbent (FAVOR 880) was used in the test. The average value of AUL for all the samples was 9.6 g/g (the viscosity of all the BM samples range from 1.4 to 109.9 poise).

The fecal fluid samples were also grouped according to the viscosity of whole BM prior to separation. The low viscosity (20 poise or less) fecal fluid had an average 0.3 psi AUL value of 13.4 g/g for FAVOR 880 while medium to high viscosity (20 to 109.9 poise) fecal fluid had an average of 0.3 psi AUL of 6.7 g/g. Therefore, there is a correlation between the fecal fluid AUL value and the original viscosity of whole BM. This is probably caused by the difference in the soluble material content in the samples. The high viscosity samples had a high level of dissolved proteins, carbohydrates, etc. These dissolved components also contribute to the depression of AUL by fecal fluid. This was illustrated by the component effect data disclosed in the next section.

With these determined targets, it was possible to proceed to the next step in the invention of a fecal fluid simulant.

B. Determination of the Effect of Fecal Fluid Components on the Absorbency

In order to develop a fecal fluid simulant, it was important to determine the quantitative effect of the individual component on the absorbency.

1. Effect of Protein

The proteins from both natural and synthetic origins can be used. An example of natural protein is egg white. Egg white can be separated into two fractions: a thin egg white fraction of low molecular weight and low viscosity, and thick egg white fraction of high viscosity and containing mucin.

Synthetic proteins prepared by polymerization of a variety of amino acids using protein synthesizer (employing Meerifiled's peptide synthesis process) can be utilized. The synthetic proteins have precise chemical composition and amino acid sequence but they are costly to make and less available.

For this invention, various egg components were separated and used as model compounds for protein. The egg components had the advantages of being biologically produced, low cost and safe to use.

The 0.3 psi fecal fluid AUL of pure egg components were determined to be as follows:

Thin egg white: 4.3 g/g

Thick egg white: 3.2 g/g

Egg yolk: 4.1 g/g

To determine the effect of egg protein on AUL, a series of solutions containing proteins were made. These solutions had egg protein concentrations in the range of protein content in the collected infant fecal fluids. Three concentration levels were selected: 1.4% (representing the low end of protein content of collected fecal fluids); 2.3% (representing the average of the protein content of collected fecal fluids), and 3.0% (representing the high end of the protein concentration of collected fecal fluids).

The solutions were based on 0.9% saline. Since egg whites contain water, an egg protein solution of certain protein concentration and salt concentration was needed.

The proper concentration was determined by first determining the water content of egg component using a moisture analyzer. The water content was then translated into the protein content in each egg component. The water in the egg component was taken into consideration when egg protein was added to the solution. The water in egg will cause a dilution in sodium chloride content. Additional sodium chloride was added to the solution based on the compositional calculation to obtain a composition of base ingredients going into the solution.

The effect of thin egg white protein on the absorbency of FAVOR 880 was determined. Thin egg white contains low molecular weight protein. It does not contain the high viscosity mucin. The FAUZL (free absorbency under zero load) decreased slightly with the increasing thin egg white protein. The fecal fluid AUL at 0.3 psi decreased substantially with increasing egg white protein, from 28.5 to 13.6 g/g.

The effect of thick egg white protein on both the FAUZL and AUL was determined. Thick egg white contains the high viscosity mucin component. The thick egg white decreased the fecal fluid AUL values more severely than the thin egg white at the same protein concentration. The relationship was used in developing the fecal fluid simulant.

2. Effect of Carbohydrates on the Absorbency

The effect of carbohydrates on fecal fluid AUL and FAUZL was determined by making testing fluid containing model carbohydrates. All the experiments were performed in 0.9% saline. There was little effect on absorbency resulting from carbohydrates.

The effect of sucrose (formed from two glucose units) on fecal fluid AUL and FAUZL was determined. The effect of this carbohydrate on both FAUZL and fecal fluid AUL was minimal. The effect of corn syrup on absorbency was determined. The effect was also negligible on both fecal fluid AUL and FAUZL.

Among the carbohydrates studied, the only carbohydrate having a substantial effect on the absorbency was dextran. Dextran is a bacterially produced polysaccharide from sucrose. It has different molecular weights depending on the bacteria strains and conditions of collected fecal fluid. It was found that the FAUZL was reduced from 36.2 g/g for FAVOR 880 in saline to 25.8 g/g at 12% concentration (the high end of determined carbohydrates in fecal fluid). The fecal fluid AUL was decreased from 28.5 g/g for saline to 19.1 g/g for 12% dextran solution.

3. Effect of Fat on Absorbency

When emulsified corn oil (used as a fat simulant) was added to the saline solution, it was found that the fat had little effect on either fecal fluid values.

C. Fecal Fluid Simulant Formulations

Based on the above relationship between the fecal fluid component and the determined absorbency, a series of formulation experiments were performed to develop a viable fecal fluid simulant with properties similar to the "real" biologically produced fecal fluid.

The fecal fluid AUL of saline, low viscosity fecal fluid, medium to high viscosity fecal fluid, and various egg components were determined. The real fecal fluid had AUL values between those of 0.9% saline and the egg components.

A series of formulations were designed based on calculation of the fecal fluid component effect at different concentrations. It was found that both natural and synthetic carbohydrates can be used. Low molecular weight carbohydrates, carbohydrate oligomers, and high molecular weight carbohydrates can be used in the formulation of the fecal fluid simulant.

4. Embodiments of Fecal Fluid Simulants

The fecal fluid simulants comprise proteins, carbohydrates, salt and water. Proteins from various origins and different preparation methods can be used for this invention. Proteins separated from eggs such as thin egg white, thick egg white, egg yolk, mixtures of egg white and yolk, and plasma separated from human blood or animal blood can be used as the protein component in the fecal fluid simulants. The range of protein ranges from 0.1 percent to 10% by weight of the simulant.

Various carbohydrates can also be used in the formulations. The amount of carbohydrates range from 0.1 to 15% by weight. The preferred carbohydrate is dextran.

Salts of monovalent, divalent and multi-valent metal ions and inorganic anions can be used in this invention. Examples of metal ions are sodium, potassium, lithium, magnesium, calcium ions, etc. Examples of inorganic anions are chloride, bromide, fluorides, sulfate, sulfonate, phosphate, carbonate, etc. The amount of the salt level can be adjusted to the average level of salt found in the fecal fluids.

The fecal fluid simulant formulation can be based on both saline or distilled water. In the case of distilled water, additional salts are used to adjust the ionic strength of real fecal fluid.

The resulting fecal fluid is homogeneous without any observable phase separation. The resulting fecal fluid typically has a light yellow color.

The stability of the fecal fluid simulant can be substantially increased by adding preservatives.

Example of Simulant

In a 1 liter PYREX glass beaker, 128.5 grams of a 0.90 weight percent aqueous solution of sodium chloride supplied by RICCA® Chemical Company, Arlington, Tex., (10 L bag) was added. A magnetic stirrer was placed in the beaker and set on a magnetic stirring plate (Nuova II Stir Plate, Thermolyne Corporation, a subsidiary of Sybron Corporation, Dubuque, Iowa) on medium high speed (Level 7), 0.45 grams of sodium chloride (supplied by Aldrich Chemical Company, Milwaukee, Wis.) was added to the same beaker. After the sodium chloride completely dissolved, 0.72 grams of dextran (supplied by SIGMA® Chemical Company, St. Louis, Mo.) was subsequently added to the solution. After the dextran completely dissolved, 50 grams of thin egg white was added to the solution (separated from eggs by first removing the egg yolk and then filtering the egg through a 1700-micron filter made by American Scientific Products, McGaw Park, Ill.). Once all the thin egg white was added, the solution was mixed for 20 minutes. At the end of the mixing process, the beaker was removed from the magnetic stirring plate. Some of the egg particles coagulated to form pliable, stringy or clumpy, solid white masses on the center surface of the solution. The masses were removed using a disposable metal tweezers. The process produced a visually homogeneous liquid that is a pale, golden-yellowish in color.

AUL testing was performed by placing approximately 0.160 grams of a superabsorbent FAVOR 880 from Stockhausen in an AUL cylinder with a 100-mesh screen under a pressure of 0.3 psi. The cylinder was then set directly into the test fluid. Weight gains of the superabsorbent at different times were measured by removing the cylinder from the fluid and blotting away the excess fluid with a towel.

The following fecal fluid AUL result was obtained based on the average values of two repetitions using the simulant made in this example (Low Viscosity Average 1: LVA1): Absorbency under load at 0.3 psi: 13.1 g/g.

The targeted average absorbency for real, low viscosity fecal fluid: Absorbency under load at 0.3 psi: 13.4 g/g/ (range: 11.2–17.2 g/g).

Test Procedures for Fecal Fluid Intake Test and the Fecal Fluid Flowback Test Using LVA1 Fecal Fluid Simulant 1. Test Method:
    1.1 This procedure describes the testing method used for both the Fecal Fluid Intake test and the Fecal Fluid Flowback test using LVA1 Fecal Fluid Simulant on a control absorbent core system.
2. Apparatus:
    2.1. Plastic fluid intake and flowback evaluation (FIFE) device: 3 inch diameter circle and 3/16 inch thick Plexiglas base, a tube of 3 inch in height, 1 inch in inner diameter, and 1/16 inch in thickness Plexiglas tube is attached to the center of the base.
    2.2. Mettler Toledo Scale-Model PR503 Delta Range-max 510 g, d=0.01 g/0.001 g
    2.3. Plastic Petri dish approximately 3½ inches in diameter
    2.4. Four 50 gram weights (Plexiglas disks with 1.25" diameter hole)
    2.5. 50 milliliter graduated cylinder
3. Materials and Supplies:
    3.1. LVA1 Fecal Fluid Simulant
    3.2. An absorbent core (basis weight: 677 gsm; composition: 42% of FAVOR 880 superabsorbent from Degussa (Greensboro, N.C.) and 58% of CR1654 fluff from Bowater (Greenville, S.C.); density: 0.20 g/cc) cut into 3 inch diameter circles
    3.3. Spunbond liner material cut into 3 inch diameter circles
    3.4. 2.25 osy BCW (bonded carded web) surge material cut into 3 inch diameter circles
    3.5. Blotter Paper cut into 3 inch diameter circles
    3.6. The liner material or the surge material can be changed to determine the effect of the change on fecal fluid intake rate or fecal fluid flowback
4. Procedure:
    4.1. Absorbent Core System Preparation
        4.1.1. An absorbent core is layered below a 2.25 osy BCW surge material. A layer of spunbond liner is placed on top of the surge material layer.
        4.1.2. Diecut the layered material into 3 inch diameter circles. The surge material and the spunbond liner should cover the entire top surface of the core.
        4.1.3. Once the core system has been diecut, they should be compacted using a press. A gap of approximately 1.5 centimeters should be set between the rollers on the press before the layered core is run between them. The end result should be a layered core system that has been compacted to a thickness of 5.2 mm (Use bulk tester to check).
    4.2. Fecal Fluid Intake Test and Fecal Fluid Flowback Test Setup
        4.2.1. Place the core system into a plastic Petri dish (Approximately 3½ inches in diameter), and cover the core system with the plastic FIFE device.
        4.2.2. When the device is centered atop of the core place four 50 gram Plexiglas disks on top of the device. The Plexiglas disks will evenly distribute the weight.
        4.2.3. Measure twenty milliliters of LVA1 Fecal Fluid Simulant into a 50 milliliter graduated cylinder.
    4.3. Fecal Fluid Intake Test
        4.3.1. Pour the 20 milliliters of simulant into the center of the FIFE device onto the core. Pour the simulant at a constant rate and do not allow any simulant to run down the sides of the device so the results are not skewed.
        4.3.2. Start a timer at the exact moment the simulant hits the layered core material.
        4.3.3. When all 20 milliliters is poured into the FIFE device observe how long it takes for the fluid to become absorbed by the core system.
        4.3.4. When the simulant level becomes low in the tube there will be a little ring of fluid left around the edge of the center part of the device. At the moment the little ring of fluid is absorbed record the time in seconds, which have passed since the timer was first started. DO NOT STOP THE TIMER.
        4.3.5. Note: The intake rate for the control core system (described in section 3.2) has been approximately 0.36 cc/sec in the past. If the intake rate is significantly different from this run a few more core systems through the press increasing or decreasing the gap between the rollers until a core is produced that absorbs the LVA1 Fecal Fluid Simulant at the proper rate.
    4.4. Fecal Fluid Flowback Test
        4.4.1. Place six pieces of blotter paper cut to 3 inches in diameter on the digital scale and record the weight.
        4.4.2. Next wait until fifteen minutes has passed when the timer was first started during the FIFE portion of the test.
        4.4.3. At the fifteen minute mark remove the four 50 gram disks and the FIFE device from the top of the core system. Place the six pieces of blotter paper on top of the core system.
        4.4.4. Place a 50 gram disk on top of the blotter paper. Then place the 1294.51 gram weight on top of the 50 gram disk. The total weight on top of the FIFE device above the core system should measure approximately 0.6 psi.
        4.4.5. After three minutes has passed with the 0.6 psi weight atop of the FIFE device remove the weights along with the FIFE device.
        4.4.6. Weigh and record the weight of the six pieces of blotter paper.
        4.4.7. Subtract the weight of the blotter paper recorded before the flowback portion of the test from the weight of the blotter paper after the test has been completed. This will give the amount of fecal fluid flowback in grams. The average of the fecal fluid flowback values is reported.

Test Procedure for Determining Contact Area

The contact surface areas of the nonwoven materials Examples can be measured as provided below. The test equipment included: a 3"×4" (7.6 cm×10.2 cm) sample stage with minimum thickness of ¼" inch (6.35 mm), a 12.25"× 5"×3/16" (31 cm×12.7 cm×0.48 cm) piece of LUCITE®, a sample of each material cut into 3"×4" (7.6 cm×10.2 cm) rectangle, a bulk compressometer, a thermometer, a fine pen, transparency paper cut to a 3"×4" (7.6 cm×10.2 cm) rectangle, and an rH gauge (hygrometer). All contact areas that were measured using this procedure are nominal contact areas. That is the contact areas are defined by the contact that the surface features have with a flat surface resting on the features. This is not the sum of the individual fiber areas that are technically in contact with the flat surface over the projected area of the sample but include the areas between the individual fibers.

Initial Measurement and Setup

1) Perform test in a controlled environment of 74±4° F. (23.3±2.2° C.) and 50+/−10% rH.
2) Samples shall be prepared from materials that are representative of materials produced as they are removed from the forming line and before they are wound or packaged.
3) Samples are to be cut from sections of the web that are uniform and representative of the parent material.
4) Three 3"×4" (7.6 cm×10.2 cm) rectangular samples are cut from the parent material of each Example.
5) The initial bulk of each sample is measured using a bulk compressometer.
6) A load is applied and when the reading is stable for 4 seconds the value is recorded. The sample is immediately removed from the load after the value is recorded.

Initial Contact Surface/Area

7) The 3"×4" (7.6 cm×10.2 cm) sample stage is placed on top of a flat, level surface.
8) The 3"×4" (7.6 cm×10.2 cm) sample is then lined with the stage and placed on top.
9) An initial surface contact area is taken by placing a flat, clear surface over the top of the sample. A piece of transparency paper was used for this method.
10) The material provides a load of less than 0.003 psi on the material for the initial reading.
11) From the perspective directly above each contacting topographic surface feature, the perimeter of surface contact is recorded for the materials by tracing the perimeter with a fine pen.
12) The area of the material contacting the flat surface is then recorded as the initial contact area. This area is determined from the tracing performed in step 11.
13) This initial contact area is divided by the projected area of the sample (i.e. 12 square inches) to give a percentage of contact surface/area for the sample.

Contact Surface Under Increased Load

14) For additional contact area measurements under heavier loads, a flat rectangular piece of Lucite® material is placed over the sample material.
15) The center of the rectangular piece of Lucite® material is measured.
16) A 3"×4" (7.6 cm×10.2 cm) rectangle has been centered on the rectangular piece of Lucite® material and traced. The edges of the traced perimeter are parallel to the edges of the Lucite® material rectangle.
17) The Lucite® material is 12.25"×5"×3/16" (31 cm×12.7 cm×0.48 cm) in dimension and weighs 0.6 lbs (273 grams).
18) A piece of transparency paper is placed over the Lucite material so that the perimeter of the features may be recorded on the paper.
19) From the perspective directly above each contacting topographic surface feature, the perimeter of surface contact is recorded using a fine pen for the materials.
20) The area of the material contacting the flat surface is then recorded for the material and the load condition is also recorded.
21) This contact area under load is divided by the projected area of the sample (i.e. 12 inch$^2$ or 77.4 cm$^2$) to give a percentage of contact surface/area for the sample.
22) The average true load that the surface features experience is determined by dividing the weight the plate exerts on the sample by the area of the sample in contact with the flat load. E.g. 0.6 lbs on a 12 inch$^2$ sample that has 20% contact area would show a 20% contact area at a pressure of 0.25 psi [0.6 lbs/(12 inch$^2$×20%)].

Additional contact area measurements were made using two different weights, 1.2 lbs and 6 lbs (0.545 and 2.73 kg). The contact area is measured until the weight equaled 6 lbs or the contact area is greater than 90 percent.

23) A flat rectangular piece of Lucite® material is placed over the sample material.
24) The center of the rectangular piece of Lucite® material is measured determined.
25) A 3"×4" (7.6 cm×10.2 cm) rectangle has been centered on the rectangular piece of Lucite® and traced. The edges of the traced perimeter are parallel to the edges of the Lucite® rectangle.
26) The Lucite® is 12.25"×5"×3/16" (31 cm×12.7 cm×0.48 cm) in dimension and weighs 0.6 lbs (273 grams).
27) On the edges of the Lucite® material 0.3 lbs (136.35 grams) of weight are added on each end to provide a total weight of 1.2 lbs of force being placed on the 12 inch$^2$ web.
28) A piece of transparency paper is placed over the Lucite material so that the perimeter of the features may be recorded on the paper.
29) From the perspective directly above each contacting topographic surface feature, the perimeter of surface contact is recorded using a fine pen for the materials.
30) The area of the material contacting the flat surface is then recorded for the material and the load condition is also recorded.
31) This contact area under load is divided by the projected area of the sample (i.e. 12 inch$^2$) to give a percentage of contact surface/area for the sample.
32) The average true load that the surface features experience is determined by dividing the weight the plate exerts on the sample by the area of the sample in contact with the flat load. E.g. 6 lbs on a 12 inch$^2$ sample that has 20% contact area would show a 20% contact area at a pressure of 2. 5 psi [0.6 lbs/(12 inch$^2$×20%)].
33) Repeat steps 22–30 where step 26 is modified to provide a weight of 2.7 lbs (1227 grams) on each side for a total load of 6 lbs (2.72 kg).
34) Perform experiment until either the total load on the sample equals 6 lbs or the nominal contact area that the sample has with the flat material is greater than 90 percent.
35) Take and record the material's (web's) bulk at most 5 minutes after step 29.

Pressure Applied to Web ($P_w$)

Figure 2:
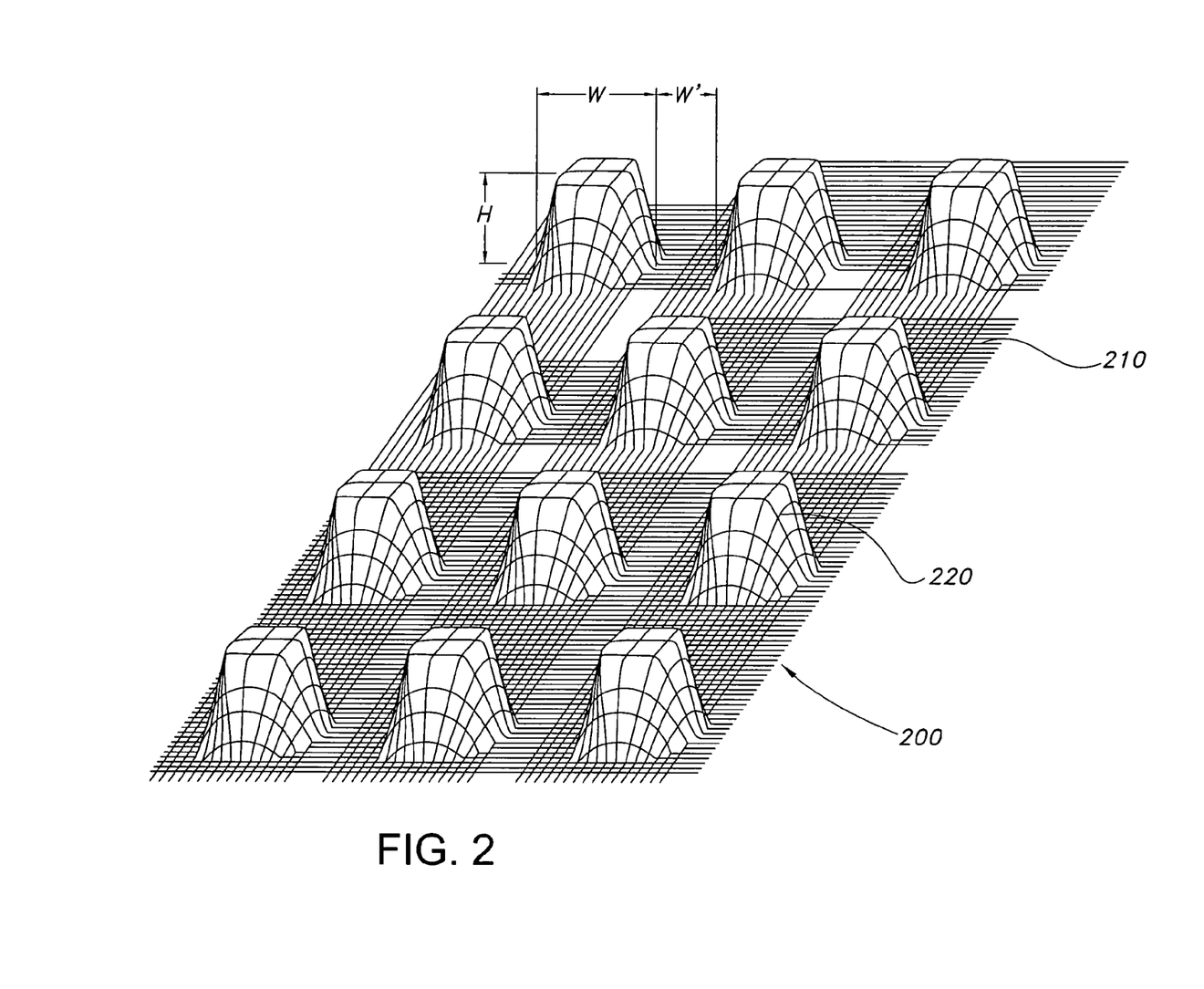
FIG. 2 schematically illustrates a portion of an exemplary bodyside liner in accordance with the present invention.
Figure 2A:
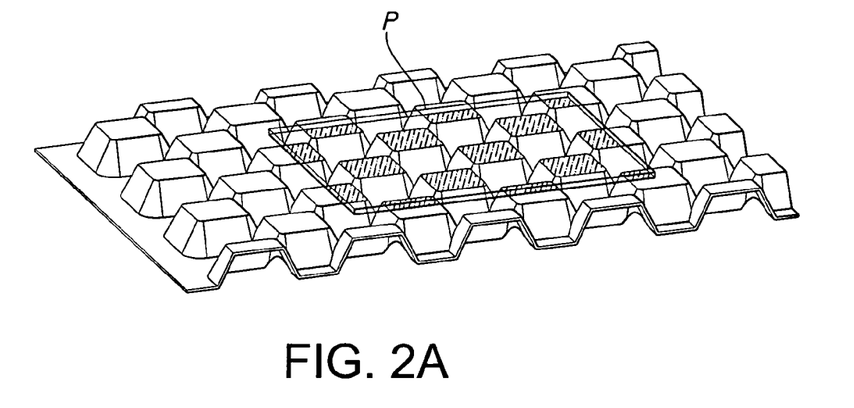
FIG. 2A is a perspective view of a substantially planar article supported on a material for the purposes of measuring contact area of the material.
Figure 2B:
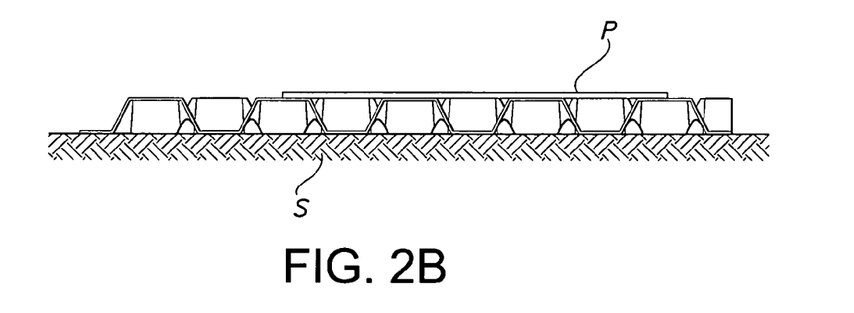
FIG. 2B is a cross-sectional view of a substantially planar article supported on a material for the purposes of measuring contact area of the material.
Figure 2C:
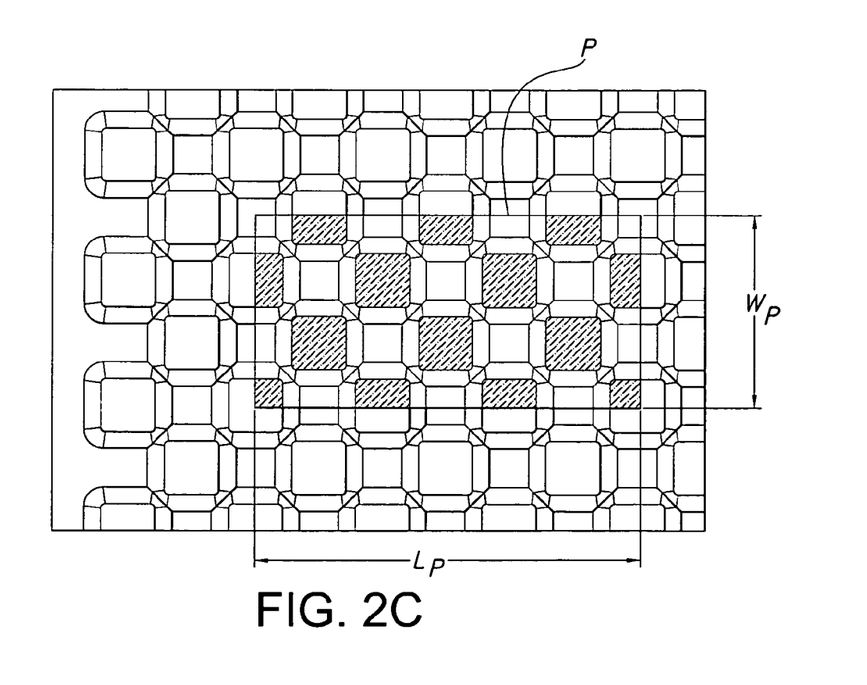
FIG. 2C is a top-side plan view of a substantially planar article supported on a material for the purposes of measuring contact area of the material.

Referring to FIG. 2A, the contact area of object P with the nonwoven is is the sum of the cross-hatched areas shown in FIGS. 2A and 2C. The pressure that an object P supported by features transmits to a nonwoven web is measured by dividing the weight of the supported object P by the flat contiguous area that connects all of the points of the sheet that directly contact the article. For example, if an object is supported by sixteen macroscopic features, then the area of the nonwoven web supporting the object P is the contiguous area ($W_p \times L_p$) measured in a plane parallel to the nonwoven base plane that connects all of the sixteen features or the parts of the sixteen features that support the object. In FIG. 2C, the pressure that an object P supported by the nonwoven transmits to the sheet is measured by dividing the weight of the supported object P by the flat contiguous area $L_p$ by $W_p$ beneath the object.

Average Pressure Observed by Surface Features ($P_f$)

The average true load that the surface features experience is determined by dividing the weight the plate exerts on the sample by the area of the sample in contact with the flat load. The average pressure observed by the surface feature $P_f$ is determined by correcting for the actual area in contact with the load $P_w$. This is done by dividing $P_w$ by the percent contact area.

DETAILED DESCRIPTION OF THE PRESENTLY PREFERRED EMBODIMENTS

The present invention provides a bodyside liner or a topsheet for a disposable, absorbent article that has a fecal fluid intake rate of greater than about 1.3 cubic centimeters per second as measured by the Fecal Fluid Intake Test, more particularly section 4.3 of the Test Procedures for Fecal Fluid Intake Test and the Fecal Fluid Flowback Test Using LVA1 Fecal Fluid Simulant described above. The present invention also provides an absorbent article, for example a diaper, with improved fecal fluid intake rate of greater than about 1.3 cubic centimeters per second as measured by the Fecal Fluid Intake Test. It is believed that the disposable absorbent article will have improved intake of other fluids, such as urine, including viscous fluids such as menses and so forth. The absorbent article may have fecal fluid intake rate of greater than about 1.4 cubic centimeters per second, more desirably greater than about 1.5, more desirably greater than about 1.8, more desirably greater than about 2 and still more desirably greater than about 2.5 cc/sec. Desirably, the absorbent article not only has an improved fecal fluid intake rate but also has a low fecal fluid flowback and more desirably low skin hydration as measured by TEWL. Generally, the present invention provides an absorbent article, for example a diaper, with an improved fecal fluid intake rate, an example of which is described below.

Figure 1:
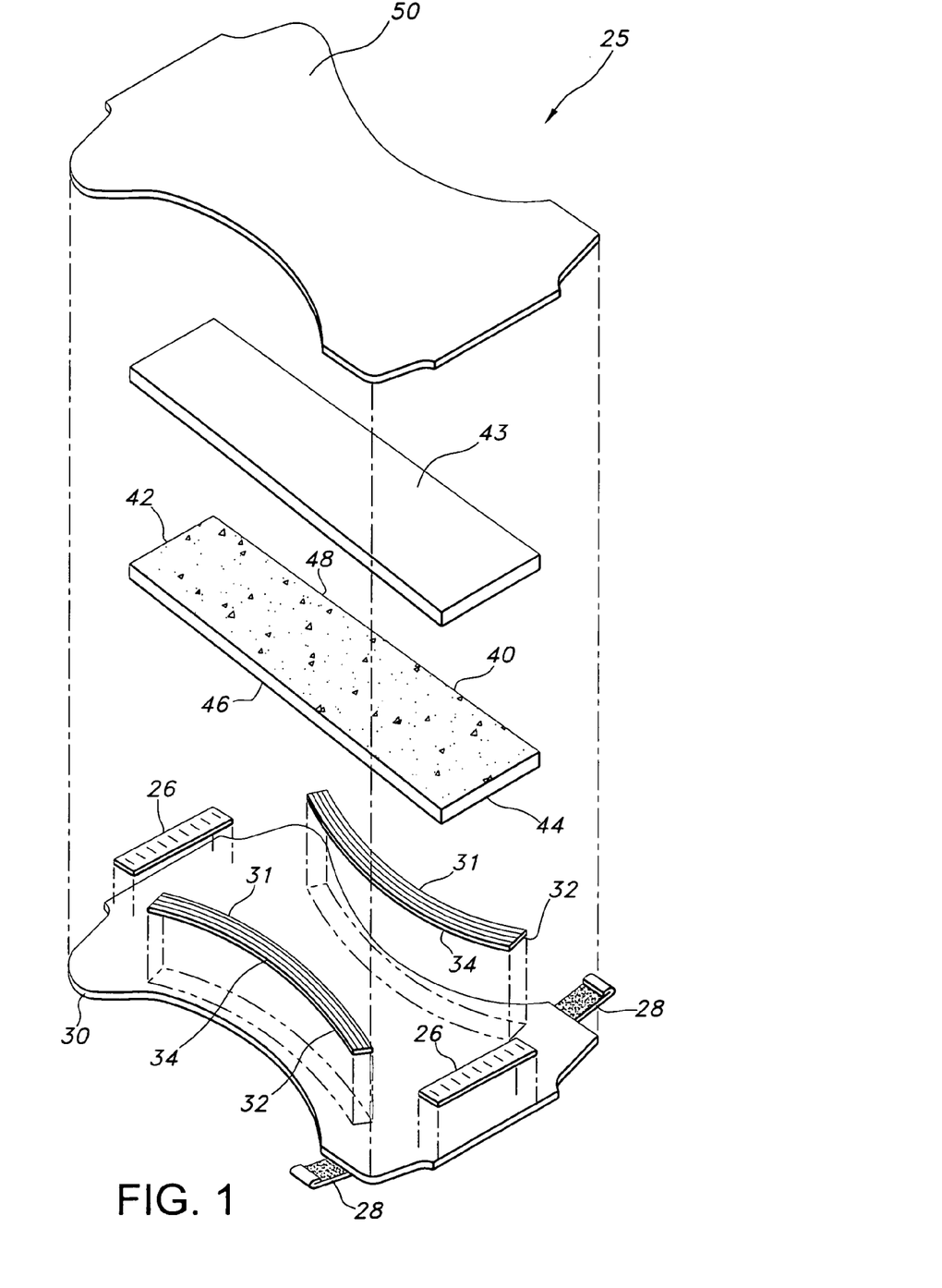
FIG. 1 is an exploded view of an absorbent article for example a diaper.

An exemplary absorbent article of the present invention, specifically an exemplary diaper, is illustrated in FIG. 1. Other disposable, absorbent articles that are considered within the absorbent articles in the present invention include, training pants, swimming pants, underpads used in nursing homes or hospitals and other incontinence articles and garments. Desirably, the diaper or other absorbent article also has a low flowback of fecal fluid. Increasing the fecal fluid intake rate of an absorbent article can reduce the probability of leakage of fecal matter, particularly runny fecal fluids and fecal matter. Reducing the fecal fluid flowback rate can reduce or eliminate the amount of runny feces and fecal fluid in contact with the skin, thus promoting skin health.

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence articles, training pants, and the like. In addition, the invention will be described in the context of its various configurations. It should be appreciated that alternative arrangements of the invention can comprise any combination of such configurations.

FIG. 1 illustrates a personal care article 25 according to the invention, in this case a disposable diaper. Disposable diaper 25 includes a liquid permeable bodyside liner 50, a surge material layer 43, an absorbent core 40, and an outer cover 30. The illustrated absorbent core 40 has a rectangular shape, and includes a front waist edge 42, a rear waist edge 44, and two longitudinal side edges 46 and 48. For purposes of the invention, the absorbent core 40 is not limited to a rectangular shape, and may have an hour glass shape, or another suitable shape. The surge layer and other layers can also have different shapes and dimensions. Diapers and various diaper are well known. Diapers, diaper constructions, diaper components and diaper designs are illustrated and described in for example U.S. Pat. No. 6,316,687 to Davis et al., U.S. Pat. No. 6,515,029 to Krzysik et al. and International Patent Application no. PCT/US03/26183, which are hereby incorporated by reference herein each in its entirety.

Referring again to FIG. 1, the other components of the personal care article 25, such as a disposable absorbent article, may be of conventional structures. Surge layer 43 is constructed from highly liquid pervious (generally non-absorbent) materials. The surge layer functions to transfer liquid from the wearer to the interior of the absorbent article. Suitable liquid pervious materials include porous woven materials, porous nonwoven materials, films with apertures, open-celled foams, and batting. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. U.S. Pat. No. 5,904,675 to Laux et al. provides further examples of suitable surge materials and is incorporated by reference herein in its entirety. Either layer may also be an apertured plastic film.

In order for the absorbent core 40 to be most effective, the upper layers of the absorbent structure (e.g., the bodyside liner 50 and surge layer 43 in FIG. 1) should each have a structure which is relatively open and receptive to the transmission of viscous fluids. Open structures include, for instance, apertured materials, open low density spunbond materials, and other open nonwoven materials.

Open structures for the upper layers provide better intake of runny feces and facilitate travel of the runny feces to a location away from the wearer's skin. These structures also help prevent leakage from the absorbent article. In one embodiment, the bodyside liner and/or surge material layers may have open structures only in those regions which superimpose the region(s) of the absorbent core designed for optimal fecal fluid absorption. For instance, the bodyside liner and/or surge layers may have open structures in regions which superimpose the back region, the crotch region, or both of the absorbent core 40. The remainder of the bodyside liner and/or surge layers may have a more conventional structure designed primarily for the intake of less viscous aqueous liquid, such as urine.

Outer cover 30 may be breathable to water vapor, and is suitably liquid impermeable. Outer cover 30 may include a breathable, substantially liquid impermeable polymer film formed by mixing a thermoplastic polyolefin with a particulate inorganic filler, and stretching the film in at least one direction to form voids around the filler particles and micropores in the film. Outer cover 30 may also include a fibrous nonwoven web, such as a polyolefin spunbond web laminated to the breathable film, to provide a soft, cloth-like texture and feel to the underside of personal care article 25. Attached to outer cover 30 are waist elastics 26, leg elastics 31, and fastening tabs 28, which may be of any conventional structure. Leg elastics 31 may include a carrier sheet 32 and individual elastic strands 34. Fastening tabs 28 may include fastening tapes or mechanical fasteners such as VELCRO® hook and loop fastening elements.

An example of a bodyside liner in accordance with an exemplary embodiment of the present invention is illustrated in FIG. 2. The exemplary bodyside liner material provides improved fecal fluid intake and may also provide decreased fecal fluid flowback as well as improved dryness as measured by TEWL. FIG. 2 schematically illustrates a bodyside liner material that was used in the Examples. The materials used for the bodyside liner were purchased from SpaceNet Inc. of Monroe, N.C. These materials are marketed as a cushioning material under the trademark SPACENET. The SPACENET materials have an open-mesh structure having filigree like appearance. Desirably, the bodyside liner or topsheet material have large open volumes and allow the free passage of air, aqueous liquids and other fluids. Air flows through these materials are at least 3000 cubic feet per minute (cfm) or about 85 liters per minute at 125 Pascals of pressure as measured by ASTM D 737-96 and may even exceed the upper limits of the standard Frazier air permeability test. SPACENET materials are available in different sizes and patterns under the material designations K15003, K15005 and K30008. The SPACENET materials are a synthetic thermoplastic fiber network of fibers and have topographical features as illustrated and described in U.S. Pat. Nos. 5,731,062, 5,851,930 and 6,007,898 and typically have from 90 to 99 percent open area. Desirable materials have an open area of greater than about 50 percent, more desirably greater than 55 percent open area and even more desirably greater than 60 percent.

Advantageously, the bodyside liner material provides support for the body, for example an infant wearing a diaper incorporating the bodyside liner material as the body contacting surface. The topographical features of the exemplary network are resilient and can minimize contact of a wearer's skin with a liner and underlying absorbent structure(s) in a diaper or other disposable, absorbent article that includes such a network as a bodyside liner or topsheet. It is believed that the "land" areas or recesses between topographical features allow for runny bowel movement to reside in these lower areas and away from a wearer's skin. The topographical features may also deter the movement of feces across the liner surface thus minimizing the spread of fecal matter. This is advantageous because it may provide for a smaller spreading pattern and minimize the contact area of the fecal matter with the skin of a wearer of the absorbent article. Desirably, the bodyside liner has projections and optional depressions or other structures which are compressible and return to the original shapes to provide separation between a wearer and absorbent structures below the bodyside liner. Additionally, the predominance of large pores and the absence of small pores in these exemplary materials eliminate capillary moisture entrapment and the maximum water pick up of these materials can be in the order or 1 percent or so. The low moisture uptake and high airflow also combine to allow very rapid drying.

Desirably, the bodyside liner includes one or more topographical features that minimize contact between the liner and a wearer of an article including the bodyside liner. Thicknesses under compression of various materials were determined using a cyclical testing procedure to measure pressure at a compressed thickness. In particular, a 3 cycle compression testing was performed measuring force versus displacement. For this test, the sample size was 3 inches square with the protrusions of the test material facing upward. The surface used to contact the sample was a 1" diameter circle of the testing unit. The initial gauge separation was 4 centimeters and did not contact the surface of the sample. The test lowered the cross-head at 5 mm/sec (11.8 inches/min) until a force of 360 grams (~1 psi pressure) was reached then immediately without pause returned to the zero point, i.e., the 4 cm gauge separation, unloading at the same cross-head speed to the starting 4 cm height. The test repeated the cycle for a sample up to 3 times. The testing was done on a TA-XT2 Texture Analyser from Stable Micro Systems using Texture Expert V1.22 software. The tests were conducted under ambient temperature and humidity room conditions. For example, a topographical feature of the exemplary SPACENET K15003 liner compresses to only about 3 millimeters, about 75 percent of its unstressed height which is about 4 millimeter when compressed with a pressure $P_w$ of about 0.2 psi. A topographical feature of the exemplary SPACENET K15003 liner compress to only about 2 millimeters, about 50 percent of its unstressed height when a compressive force of about 0.4 psi is exerted on the web. And, a topographical feature of the exemplary SPACENET K15003 liner may compress to only about 1 millimeters when a pressure of about 0.5 psi is exerted on the web. Bodyside liners of the present invention may include one or more macroscopic features that provide at least 0.08 cubic centimeters of air space, 0.09 cubic centimeters of air space and even greater than 0.10 cubic centimeters of air space per square centimeter between the top surface of the nonwoven web and an article resting on the macroscopic surface feature at a 0.3450 kPa load on the web ($P_w$). The practices used for determining these values are detailed in the methods section. For the purposes of describing the resiliency of surface features, the average pressure exerted on a surface feature is denoted $P_f$. For the purposes of material characterization of the web and techniques used for bulk compressometry a different pressure is reported. This is the pressure exerted on the web or $P_w$. $P_w$ is the pressure that would be exerted on a flat material having 100 percent contact with the load or force.

Turning to FIG. 2, the exemplary material is a woven network of polyester fibers 200 that is thermoformed into a pattern having topographical features 220 of approximately 9.5 millimeters in diameter and 6.3 millimeters in height. Suggested heights of topographical features range from about 2 millimeters to about 10 millimeters, more desirably at least 3 millimeters. Suggested distances between adjacent topographical features are at least about 2 millimeters. Suggested materials have apertures as well a topographical features. Suggested sizes for the apertures range from about 0.25 millimeters to about 5 millimeters in equivalent diameter.

The woven network is very open and resilient. Both properties are desirable for enhancing dryness. Desirably, the network has adequate resiliency to recover its structure and/or height after a pressure typically experienced during use is applied and released. The high permeability of the open structure allows fluids to penetrate into the absorbent structure(s) below, for example the surge management layer and the absorbent core while the resiliency provides enough skin separation to further enhance dryness. The polyester fibers are relatively hydrophobic further enhancing dryness. The topographical features 220 of this material are arranged in a repeating pattern as illustrated in FIG. 2 and are spaced apart from each other by land areas 210 that are approximately ¼ of an inch in width. The SPACENET material is a rigid three-dimensionally shaped fiber network structure that is highly air permeable and liquid permeable. Desirably, this exemplary material is soft and highly resilient. Desirably, the network structure is deformable and exhibits high post-yield dimensional recovery. For example, these exemplary materials can recover their original thickness dimensions when compressed beyond 10 percent and some when compressed beyond 20 percent of their thickness. Advantageously, these materials recover their network heights when the compressive stress is removed and the more desirable structures recover their shapes after being compressed to 50 percent of their original heights or thicknesses and can be repeatedly compressed without losing their springiness. Structurally, the illustrated network of the exemplary material includes a plurality of "hat-shaped" projections 220 arranged in a two-dimensional array along the width and length of the material over a base area 210. The network can be formed from polyester fibers or other fibers that are woven and then thermoformed in a pattern having macroscopic surface features and the shapes of the features can vary. For example, the features can be shaped like truncated cones, or more round, triangular, square, rectangular, pentagonal and so forth. The stiffness and the load-bearing capabilities of the network can be varied by varying the sizes, heights and shapes of the surface features, the pattern of the features, the stiffness of the individual fibers and/or by varying the strength of the crossover bonds of the fibers in the network. The stiffness of the fibers can be varied by varying the fiber composition, the fiber diameter, the fiber cross-section and the level of molecular orientation of the fibers among others as described in U.S. Pat. No. 5,851,930. Other potential materials are illustrated and described and illustrated in U.S. Pat. Nos. 5,158,821 and 5,364,686.

The suggested SPACENET materials have uniform permeability throughout to evenly allow air and/or liquids to flow through the material and to any absorbent structures below the material. As previously stated, the sizes, heights, shapes and spacings of the pattern of projections 220 of the material can vary and any number of patterned surface features may be present as long as the material provides adequate permeability and separation. Although the surface 200 having surface features 220 is illustrated as a surface having features uniformly distributed in both the machine direction (MD) and the cross direction (CD), the features can be uniformly distributed in only one direction, either the machine direction or the cross direction, or in no direction. Also, for example, the features 220 do not necessarily have to be uniformly provided or distributed on the surface 200 and can be provided and distributed in any pattern.

In the exemplary embodiment, the SPACENET material 200 was used as a top sheet in a diaper. As previously stated, the SPACENET material advantageously has uniform permeability throughout and allows uniform and high air and/or liquid flow through the material to the absorbent structure(s) below. Unexpectedly, the liner material also provides improved fecal intake and may limit or otherwise reduce the spreading of fecal matter during use. The high, uniform permeability of the SPACENET material is particularly desirable. It is envisioned that other woven and nonwoven materials with high permeability can be used. Desirably, the surface and surface features have a uniform open area that desirably has an percentage of open area that is greater than 10 percent, more desirably having more than 15 percent open area and even more than 20 percent open area. The surface and surface features may have uniform permeability, desirably greater than 300 cubic feet per minute (cfm) and more desirably 500 cfm and greater. It would also be desirable to provide a surface including such features that is strong enough and durable enough to handle the requirements of repeated use and are capable of recovering all or part of the network thickness during normal use, for example supporting the weight of an infant wearing a diaper including such a material.

Generally, the bodyside liner may include any number, size and/or pattern of surface features. The surface features may include projections and/or recesses. It is desirable that the surface features are foraminous and permeable to gas. Generally, the surface features 220 of the forming surface 200 are separated by land areas 210 as illustrated in FIG. 2. The surface features 220 have a cross-section width (W), which extends between adjacent land areas 210 and form part of the reference surface area. The surface features 220 have a minimum dimension, for example, a height (H), a depth, a length or a width (W), of at least about ⅛ of an inch, ⁵⁄₃₂ of an inch, ³⁄₁₆ of an inch and even exceeding ¼ of an inch. The bodyside liner may include projections or depressions that have a minimal dimension W which is at least about ⅛ of an inch, ⁵⁄₃₂ of an inch, ³⁄₁₆ of an inch and even exceeding ¼ of an inch. The cross-sectional areas of the projections of the bodyside liner desirably total from about 10 percent to about 95 percent of the referenced surface area of the fabric, and more desirably from about 20 percent to about 50 percent of the reference surface area of the fabric thus decreasing the contact area of a body with a fabric of the invention.

In one particular embodiment, the present invention includes a nonwoven structure having macroscopic surface features that can be used to separate one surface from another surface, for example, a baby's bottom from an absorbent layer of a diaper. In several desirable embodiments, the structure has physical, aesthetic, and functional attributes that are particularly desirable for use as a bodyside liner in disposable absorbent products such as: diapers; training pants; incontinent pads; feminine hygiene products such as feminine pads, sanitary napkins, and pantiliners; and so forth.

EXAMPLE 1

A modified diaper in accordance with the present invention was constructed by removing the standard bodyside liner from a HUGGIES® UltraTrim Step 3 diaper and substituting a section of SPACENET K15003 material for the topsheet that was removed. HUGGIES® UltraTrim Step 3 diapers are commercially available from Kimberly-Clark Corporation. The HUGGIES® UltraTrim Step 3 diaper consisted of an outercover having a breathability of 12,000 Mocon, 0.8 osy SMS spacer layer, a 20 osy absorbent layer that consisted of 40 weight percent of superabsorbent material and 60 weight percent of fluff, a 2.5 osy through air bonded carded web surge layer and a 0.5 osy polypropylene spunbond liner The SPACENET K15003 material was K15003 obtained from SpaceNet, Inc. of Monroe, N.C. and consisted of a woven network of 150-micron poly(ethylene terephthalate) fibers having topographical features as illustrated in FIG. 2 and having heights of about ¼ of an inch. The SPACENET K15003 material cut to the dimensions of the topsheet that was removed. The cut SPACENET K15003 material was substituted with the hills side up for the removed conventional spunbond liner. The SPACENET liner was taped in the place of the removed liner and then tested for dryness as measured by TEWL on the forearms of adult female subjects to measure the amount of evaporative water loss during simulated use. The TEWL of this hand-modified example in accordance with the present invention was 15.25 g/m$^2$/hour versus 21.81 g/m$^2$/hr for the same diaper structure with a conventional topsheet. The reduction in TEWL was about 30 percent. It is believed that the topography of this Example 1 liner provided a separation between the wetness of the underlying absorbent structures of the modified diaper and the skin allowing for a drier environment. A reduction in TEWL is significant because lower TEWL values are an indication of improved dryness which may improve skin health.

EXAMPLE 2

An additional example in accordance of the present invention was prepared by forming a composite of SPACENET K15003 material as a liner, over a 2.5 osy surge management layer over a 20 osy absorbent core of 42 weight percent superabsorbent particles (SAM) and 58 weight percent fluff. The composite approximating the structure of a diaper of the present invention was measured for fecal fluid intake and fecal fluid flowback as described in the Test Procedures for Fecal Fluid Intake Test and the Fecal Fluid Flowback Test Using LVA1 Fecal Fluid Simulant described above. The FIFE test data for this example and other comparative examples are presented in Table 1 below. The FIFE intake rate of the tested commercially available products ranged from about 0.3 to about 1.2 cc/second. The composite structure of this example had a surprisingly high intake rate of about 2.8 cc/second. The intake of the composite structure was more than two and half times higher than the intake rate of the closest commercially available diaper.

TABLE 1

Intake Results of Absorbent Systems Using the Fecal Fluid Intake Test Of Section 4.3

| Example number or description of structure or diaper tested | Fecal Fluid Intake Rate (cc/sec) |
| --- | --- |
| Example no. 2 SPACENET liner, 2.5 osy surge and 42/58 absorbent core | 2.780 |
| Comparative Example A - PAMPERS ® New Baby diaper | 1.119 |
| Comparative Example B - DRYPERS ® diaper with surge | 0.661 |
| Comparative Example C - PAMPERS ® Swaddlers diaper | 0.500 |
| 0.5 osy spunbond polypropylene liner, 2.5 osy surge 42/58 core | 0.533 |

The composite structure of Example 2 was tested for fluid flowback using the Test Procedure For The Liner Penetration Test Using 7-3 BM Simulant described above. Comparative examples were also tested. The fluid flowback data for Example 2 and the comparative examples is presented in Table 2 below.

TABLE 2

Flowback of Absorbent Systems and Various Commercial Diapers Using the Fecal Fluid Flowback Test of Section 4.4

| Example number or description of structure or diaper tested | Fecal Fluid Flowback (g) |
| --- | --- |
| Example no. 2 SPACENET liner, 2.5 osy surge and 42/58 absorbent core | 0.0505 |
| Comparative Example A - PAMPERS ® New Baby diaper | 0.1275 |
| Comparative Example B - DRYPERS ® diaper with surge | 0.159 |
| Comparative Example C - PAMPERS ® Swaddlers diaper | 0.057 |

The composite structure of Example 2 had low fecal fluid flowback as well as improved fecal fluid intake rate. Specifically, Example 2 had low fecal fluid flowback and a fecal fluid intake rate that was twice the fecal fluid intake rate of the diaper with the next highest intake rate. Thus, in another embodiment the present invention provides a diaper or other disposable absorbent article that has a low fecal fluid flowback as well as improved fecal fluid intake rates. Absorbent articles of the present invention can have fecal flowback as low as 0.05 grams. In still yet another embodiment, the present invention provides a disposable absorbent article that has an improved fecal fluid intake rate as well as low TEWL.

While the invention has been described in detail with respect to specific embodiments thereof, it will be appreciated that those skilled in the art, upon attaining an understanding of the foregoing may readily conceive of alterations to, variations of and equivalents to these embodiments without departing from the spirit and scope of the invention. Accordingly, the scope of the present invention should be assessed as that of the appended claims and any equivalents thereto.

We claim:

1. A disposable absorbent article for the absorption and containment of urine or other body exudates, the disposable absorbent article comprising:
    a. a liquid impervious backing sheet;
    b. a liquid pervious bodyside liner; and
    c. an absorbent material disposed between the liquid pervious bodyside liner and the liquid impervious backing sheet,
    wherein the bodyside liner comprises a woven network of fibers having an open area of 50–99% and defines a plurality of topographical features surrounded by land areas, the topographical features
        being oriented towards a wearer,
        projecting to a height of 2 millimeters to 10 millimeters relative to the land areas, and
        defining a cross-sectional area that is 10–95% of a bodyside liner area.

2. The disposable absorbent article of claim 1 wherein the topographicel features are spaced apart by approximately ¼ inch.

3. The disposable absorbent article of claim 1 further comprising 0.08 to 0.10 cubic centimeters of air space per square centimeter surface area between a top surface of the bodyside liner and an article resting on the top surface at 0.3450 kPa load.

4. The disposable absorbent article of claim 1 wherein the bodyside liner further comprises apertures having a size of 0.25 millimeters to 5 millimeters in equivalent diameter.

5. The disposable absorbent article of claim 1 wherein at least a portion of the disposable absorbent article has a focal fluid intake rate of 1.3 to 2.8 cubic centimeters per second as measured by the Fecal Fluid Intake Test.

6. The disposable absorbent article of claim 1 wherein the woven network of the bodyside liner comprises polyester fibers.

7. The disposable absorbent article of claim 1 wherein the bodyside liner is adapted to recover to an original thickness after compressive forces are applied and removed, the compressive forces resulting in compression of 10–50% of the original thickness.

8. The disposable absorbent article of claim 1 wherein the cross-sectional area is 20–50% of the bodyside liner area.

9. The disposable absorbent article of claim 1 wherein the bodyside liner has an open area of 90–99%.

* * * * *

UNITED STATES PATENT AND TRADEMARK OFFICE
CERTIFICATE OF CORRECTION

PATENT NO. : 7,105,716 B2  
APPLICATION NO. : 10/749627  
DATED : September 12, 2006  
INVENTOR(S) : Baratian et al.

It is certified that error appears in the above-identified patent and that said Letters Patent is hereby corrected as shown below:

In the Claims:

Claim 5, column 21, line 2, delete "focal" and substitute --fecal--

Signed and Sealed this

Sixth Day of March, 2007

JON W. DUDAS  
*Director of the United States Patent and Trademark Office*